United States Patent [19]
dePadova

[11] Patent Number: 5,753,651
[45] Date of Patent: May 19, 1998

[54] METHOD OF MODIFYING ANGIOTENSIN RECEPTOR ACTIVITY FOR MEDIATION OF PAIN

[76] Inventor: Anthony S. dePadova, 49 Dexter Dr. North, Basking Ridge, N.J. 07920

[21] Appl. No.: 727,553

[22] PCT Filed: Apr. 28, 1995

[86] PCT No.: PCT/US95/05312

§ 371 Date: Oct. 23, 1996

§ 102(e) Date: Oct. 23, 1996

[87] PCT Pub. No.: WO95/29674

PCT Pub. Date: Nov. 9, 1995

Related U.S. Application Data

[63] Continuation-in-part of Ser. No. 235,468, Apr. 29, 1994, Pat. No. 5,464,854.

[51] Int. Cl.$^6$ .................. A61K 31/54; A61K 31/44; A61K 31/41; A61K 31/415; A61K 31/40
[52] U.S. Cl. .................. 514/223.5; 514/303; 514/381; 514/394; 514/397; 514/417
[58] Field of Search .................. 514/223.5, 303, 514/381, 394, 397, 417

[56] References Cited

U.S. PATENT DOCUMENTS

| 4,912,096 | 3/1990 | Sudilovsky | 514/91 |
| 4,931,430 | 6/1990 | Sudilovsky | 514/19 |
| 5,246,943 | 9/1993 | Blankley et al. | 514/307 |

OTHER PUBLICATIONS

"Basic Neurochemistry—Molecular, Cellular, and Medical Aspects"—5th Edition, 1994; pp. 608–611.
"The Sympathetic Nervous System and Pain"; K.C. Bradley, Advances in Pain Research and Therapy, vol. 13; pp. 115–122 (1990).
"Pain and the Sympathetic Nervous System"; Michael Stanton–Hicks (1994).
"Textbook of Rheumatology—Fourth Edition—vol. I"; William N. Kelly, M.D., Edward D. Harris, Jr., M.D., Shaun Ruddy, M.D., Clement B. Sledge, M.D.; 1993, pp. 471–483.

1992 Conn's Current Therapy; pp. 1014–1017.
"Cyclical Mood Changes as in the Premenstrual Tension Syndrome During Sequential Estrogen–Progestagen Postmenopausal Replacement Therapy"; Stefan Hammarbäck, Torbjörn Bäckström, Juhani Holst, Bo von Schoultz and Sven Lyrenäs; Acta Obstet Gynecol Scand 64: 393–397; 1985; pp. 393–397.
"The effect of hysterectomy and bilateral oophorectomy in women with severe premenstrual syndrome" Robert F. Casper, MD, and Margaret T. Hearn, Ph.D.; vol. 162, No. 1; pp. 105–109. (1990).
"Reproductive Hormones Modulate Angiotensin II AT$_1$ Receptors in the Dorsomedial Arcuate Nucleus of the Female Rat"; Alicia Seltzer, Keisuke Tsutsumo, Kazuto Shigematsu and Juan M. Saavedra Endocrinology; vol. 133, No. 2, 1993; 939–941.
"The Premenstrual Syndrome—Effects of Medical Ovariectomy"; Ken N. Muse, M.D., Nancy S. Cetel, M.D., Lori A. Futterman, Ph.D., and Samuel S.C. Yen, M.D., D.Sc; vol. 311, No. 21; pp. 1345–1349 (1984).

*Primary Examiner*—Kimberly Jordan
*Attorney, Agent, or Firm*—Hoffmann & Baron, LLP

[57] ABSTRACT

The present invention relates to a method of modifying Angiotensin II subtype 1 (AT$_1$) receptor activity for the treatment of premenstrual syndrome (PMS) and the symptoms associated therewith, and further relates to a method for the treatment of acute or chronic pain mediated by the sympathetic nervous system. The treatment includes the administration of an effective amount of an AT$_1$ antagonist. AT$_1$ antagonists are drugs that are capable of blocking AT$_1$ receptors present within the body throughout the central nervous system including the hypothalamus. By blocking the AT$_1$ receptor activity, hypothalamic nerve activity, and therefore, sympathetic nerve activity are modulated. Thus, an effective method for treating sympathetically mediated pain is provided, as well as an effective method for treating PMS. The AT$_1$ antagonist can be used alone or in combination with other drug therapies, for instance, non-steroidal anti-inflammatory drugs, antidepressants, opiod drugs, angiotensin converting enzyme inhibitors, and diuretics.

14 Claims, 7 Drawing Sheets

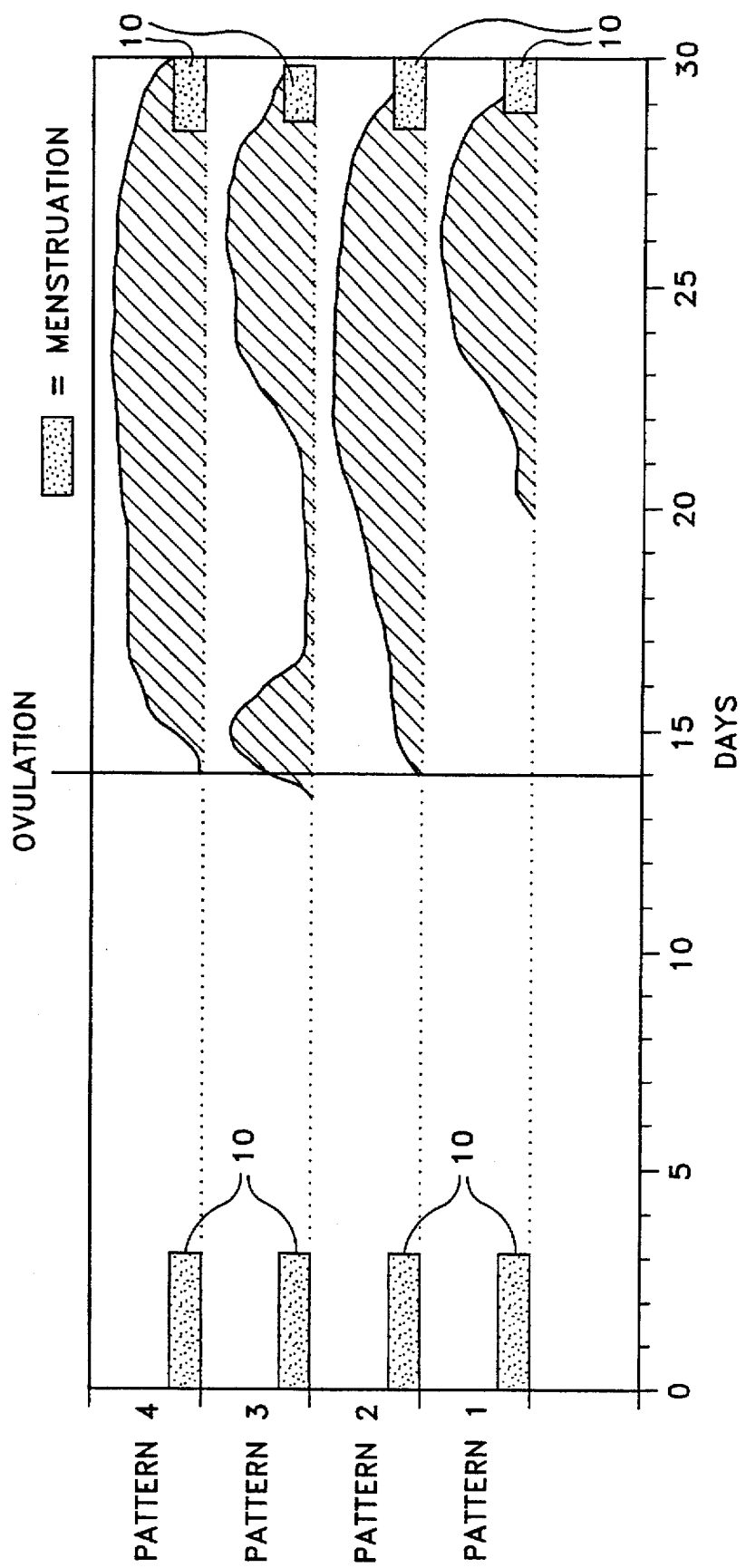

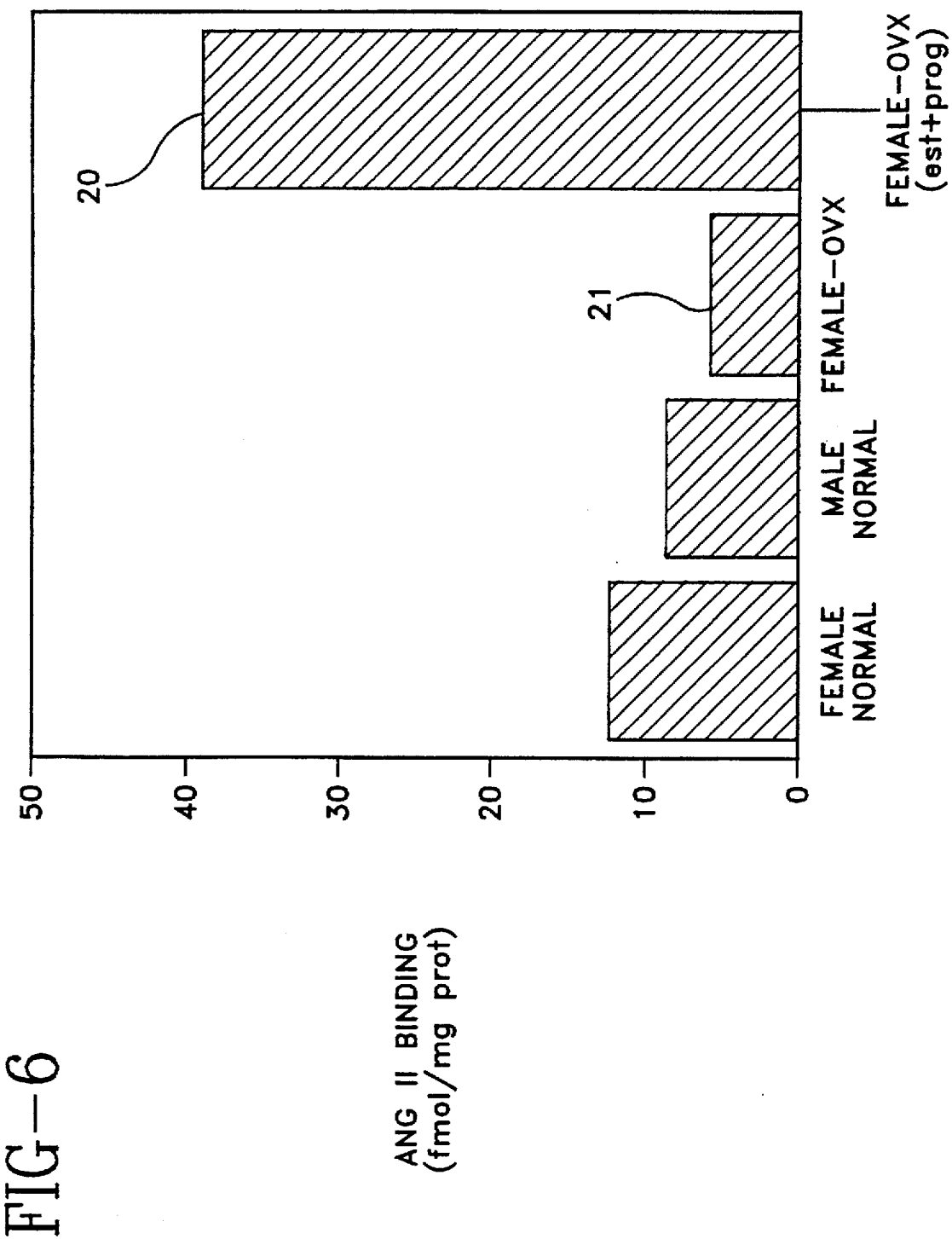

METHOD OF MODIFYING ANGIOTENSIN RECEPTOR ACTIVITY FOR MEDIATION OF PAIN

The present application is a 371 of PCT/US95/05312, filed Apr. 28, 1995, which is a continuation-in-part of U.S. Ser. No.08/235,468 filed Apr.29, 1994, now U.S. Pat. No. 5,464,854.

FIELD OF THE INVENTION

The present invention relates to a method of modifying Angiotensin II subtype 1 ($AT_1$) receptor activity for the treatment of premenstrual syndrome (PMS) and for the mediation and alleviation of pain. More specifically, the present invention relates to the use of $AT_1$ antagonists to modulate sympathetic nerve activity as treatment for pain and as treatment for PMS.

BACKGROUND OF THE INVENTION

The nervous system of the human body carries information in the form of nerve impulses to and from all parts of the body in order to regulate body activity. The nervous system consists of the central nervous system (CNS), including the brain and the spinal cord, which is responsible for integrating all activities of the nervous system; and the peripheral nervous system, including the cranial nerves and the spinal nerves, which link the receptors and the effector organs with the brain and spinal cord. The autonomic nervous system controls many bodily functions that are not consciously directed. The autonomic nervous system is subdivided into the sympathetic and the parasympathetic nervous systems, which individually control and coordinate various functions of body organs.

It is well known that the hypothalamus is an area of the brain which integrates hormonal and autonomic activity within the body, and coordinates physiological, behavioral and mood responses. The hypothalamus is the major central controller of the autonomic nervous system. Nearly every region of the brain sends signals to the hypothalamus. Pathways of nerve fibers descend from the brain and connect through synapses with areas on the brain stem, and then descend to the spinal cord where they synapse with neurons in the lateral columns of white matter which represent collections of nerve cells. There is an intimate interconnection between the nerve pathways involved in pain transmission and the sympathetic nervous system. (*Basic Neurochemistry*, Raven Press, 1994).

It is known that sympathetic functions and hypothalamic functions are partly regulated by $AT_1$ receptors. It is also known that changing levels of ovarian hormones can modify the density and function of $AT_1$ receptors, as well as induce changes in the morphology of nerve cells within the central nervous system.

At present, there are known to be two distinct Angiotensin II receptor subtypes: $AT_1$ and $AT_2$. Various drugs have been developed to block the receptor activity of the $AT_1$ and $AT_2$ receptors. Such drugs are commonly known as $AT_1$ antagonists or $AT_2$ antagonists, referring to the type of receptor which is being blocked.

U.S. Pat. No. 5,246,943 to Blankley et al. discloses novel $AT_2$ antagonists which may have utility in treating numerous disorders including those associated with pain, and may have further utility in the regulation of the menstrual cycle. $AT_1$ and $AT_2$ receptors are distinct subtypes which have different functions. Blankley recognizes this and discloses a group of $AT_2$ antagonists which have no $AT_1$ antagonist properties.

U.S. Pat. No. 4,912,096 to Sudilovsky and U.S. Pat. No. 4,931,430 to Sudilovsky et al. disclose the use of ACE inhibitors as treatment for long term chronic and acute anxiety and depressive disorders. Such disorders are distinctly different from PMS in that they are typically long-term disorders which worsen in time and require long-term systemic medication. Symptoms associated with PMS, on the other hand are intermittent, occurring during the luteal phase of the menstrual cycle and with subsequent remission. Sudilovsky specifically addresses the enkephalinase inhibitory properties of ACE inhibitors and their effects on opiod receptor activity in treating depression and anxiety. Further, the Sudilovsky references do not suggest the use of $AT_1$ antagonists.

PMS can have a debilitating effect on humans, through a variety of symptoms including changes in libido, erratic behavior, lack of emotional control, tension, mood swings, restlessness, insomnia, feelings of guilt, low self image, lack of attention span, anger, labile mood, irritability, hot flashes, cold flashes, palpitations, chills, sweating, dizziness, edema, breast tenderness, bloating, nausea, headaches, pelvic pain, abdominal pain, musculoskeletal pain and fatigue.

Further, pain can manifest itself in the human body due to a variety of reasons including acute or chronic pain associated with trauma, injury, surgery, burns, lower back disorders and arthritis, as well as various conditions including fibromyalgia, myofascial pain syndrome, chronic pain syndromes, the syndrome of menstrual migraine and pain syndrome unrelated to injury which might include symptoms such as headache, musculoskeletal pain, pain localized to one side of the body, lower back pain, complex regional pain syndrome and sympathetically maintained pain syndrome. It should also be noted that various pain syndromes can produce physical manifestations of sympathetic dysfunction, for example, Raynaud phenomenon (severe vasoconstriction of the blood vessels in the fingers), edema, numbness, paresthesia (abnormal spontaneous sensations), allodynia (pain caused by non-painful stimuli) and sweating. Therefore the sympathetic nervous system is involved in the transmission of painful impulses and plays a role in the manifestation of the aforementioned painful conditions.

Treatment for PMS has typically involved symptomatic treatment and relief, using conventional medications such as aspirin, antipyretics, diuretics, ibuprofen, and the like. However, these conventional treatments merely addressed the symptoms associated with PMS, and failed to address the underlying cause of the symptoms.

Further, effective treatment for pain has typically involved conventional medications such as morphine, which merely reduce the perception of pain by blocking the opiod pathway. Such opiod drugs can be disabling for patients, and have a variety of undesirable side effects.

As such, a need exists for a method for the treatment of premenstrual syndrome and the symptoms associated therewith, as well as for a method for the treatment or modulation of acute or chronic pain mediated by the sympathetic nervous system.

SUMMARY OF THE INVENTION

The present invention concerns a method of treating premenstrual syndrome and painful conditions by modulating the activity of $AT_1$ receptors and affecting changes in the functioning of central and peripheral components of the autonomic nervous system.

In one embodiment of the present invention, a method of treating acute or chronic pain mediated by the sympathetic nervous system is provided, which method includes administering an effective amount of an $AT_1$ antagonist. Such administration reduces the activity of the $AT_1$ receptors, thus modulating the sympathetic nerve activity and/or the hypothalamic activity.

A further embodiment of the present invention provides a method of treating sympathetically mediated pain disorders which includes administering an effective amount of an $AT_1$ antagonist.

In yet a further embodiment of the present invention, a method of treating premenstrual syndrome is provided, which includes administering to a female during the luteal phase or symptomatic period of a menstrual cycle an effective amount of an $AT_1$ antagonist.

A non-limiting list of $AT_1$ antagonists useful in the present invention include: sodium 2-(6-((2-ethyl-5,7-dimethyl-3H-imidazo(4,5-b)pyridin-3-yl)methyl)quinolin-2-yl)benzoate; 4'-((1,4'-dimethyl-2'-propyl(2,6'-bi-1H-benzimidazol)-1'-yl)methyl)-(1,1'-biphenyl)-2-carboxylic acid; 5-methyl-7-propyl-8-((2'-(1H-tetrazol-5-yl)biphenyl-4-yl)methyl)-1,2,4-triazolo(1,5-c)pyrimidin-2(3H)-one; 1-(N-(2'-(1H-tetrazol-5-yl)biphenyl-4-yl-methyl)-N-valerolylaminomethyl)cyclopentane-1-carboxylic acid; 1-((2'((i-pentyloxycarbonylamino)sulfonyl)-3-fluoro-(1,1'-biphenyl)-4-yl)methyl)-5-(2-(N-butyryl-N-pyridin-3-ylamino)propionyl)-4-ethyl-2-propyl-1H-imidazole, potassium salt; 4-ethyl-2-n-propyl-1-((2'-(1H-tetrazol-5-yl)biphenyl-4-yl) methyl)imidazole-5-carboxylic acid; 1H-Imidazole-5-carboxylic acid, 4-(pentafluoroethyl)-2-propyl-1-((2'-1H-tetrazol-5-yl)(1,1'-biphenyl)-4-yl)methyl-(CAS); 1H-imidazole-5-methanol, 2-butyl-4-chloro-1-((2'-(1H-tetrazol-5-yl)(1,1'-biphenyl)-4-yl)methyl)-, monopotassium salt (CAS); 3-((2'carboxybiphenyl-4-yl)methyl)-2-cyclopropyl-7-methyl-3H-imidazo(4,5-b)pyridine; 1H-imidazole-5-carboxylic acid, 1-((3-bromo-2-(1H-tetrazol-5-yl)phenyl)-5-benzofuranyl)methyl)-2-butyl-4-chloro-(CAS); 2-butyl-4-chloro- 1((2'-(1H-tetrazol-5-yl)(1,1'-biphenyl)-4-yl)methyl)-1H-imidazole-5-carboxylic acid,-1-(ethoxycarbonyloxy)ethylester, K+ salt; 3-methoxy-2,6-dimethyl-4-((2'-(1H-tetrazol-5-yl)-1,1'-biphenyl-4-yl) methoxy)pyridine; 6-(benzoylamino)-7-methyl-2-propyl-3-((2'-(N-(3-methyl-1-butoxy)carbonylaminosulfonyl)(1,1')-biphenyl-4-yl)methyl)-3H-imidazo(4,5-b)pyridine; 6-(N-acetyl-N-methylamino)-2-propyl-3-(2'-tetrazol-5-yl)-biphen-4-yl)methyl)quinazolin-4-(3H)-one; 1,1-dimethylethyl-2-(4'-(1-(3-(5-butyl)-2-oxo-(2-trifylphenyl)-(1,3,4)-trazolyl)methyl)biphenyl) sulfonylaminocarboxylate; 5-((3,5-dibutyl-1H-1,2,4-triazol-1-yl)methyl)-2-(2-(1H-tetrazol-5-ylphenyl))pyridine; 2-n-butyl-4-spirocyclopentane-1-(((2'-tetrazol-5-yl)biphenyl-4-yl)methyl)-2-imidazolin-5-one; 3-(2-butyl-1-(4-carboxybenzyl)-1H-imidazol-5-yl)-2-(2-thienylmethyl)-2-(E)-propenoic acid; 6-butyl-2-(2-phenylethyl)-5-((2'-(1H-tetrazol-5-yl)(1,1'-biphenyl)-4-yl)methyl)-4(1H)-Pyrimidinone; 2,7-diethyl-5-((2'-(5-tetrazolyl)biphenyl-4-yl)methyl)-5H-pyrazolo(1,5-b)(1,2,4)triazole; 1H-imidazole-5-carboxylic acid, 1-((3-bromo-2-(2-(1H-tetrazol-5yl)phenyl)-5-benzofuranyl)methyl)-2-butyl-4-chloro-(CAS); 1H-benzimidazole-7-carboxylic acid, 2-ethoxy-1-((2'-(1H-tetrazol-5-yl)(1,1'-biphenyl)-4-yl) methyl)-, 1-(((cyclohexyloxy)carbonyl)oxy)ethyl ester,- (CAS); 'methyl 2-((4-butyl-2-methyl-6-oxo-5-((2'-(1H-tetrazol-5-yl)-(1,1'-biphenyl)-4-yl)methyl)-1(6H)-pyrimidinyl)methyl)-3-thiophencarboxylate; and (S)-N-valeryl-N-((2'-(1H-tetrazol-5-yl)biphenyl-4-yl)methyl)-valine, and mixtures thereof.

The present invention contemplates the administration of the $AT_1$ antagonist by any efficacious method including orally, intravenously, intra-nasally and epidurally. The $AT_1$ antagonist is preferably administered in an amount from about 0.5 to about 800 mg over a period of about twenty-four hours.

In an alternate embodiment of the present invention, the $AT_1$ antagonist is administered in combination with a drug selected from the group consisting of a non-steroidal antiinflammatory drug, an opiod drug, an antidepressant drug, an angiotensin converting enzyme inhibitor, a diuretic, and mixtures thereof.

A non-limiting list of non-steroidal anti-inflammatory drugs contemplated for such a use includes ibuprofen, diclofenac, piroxcam, naproxen sodium, naproxen, nambumetone, etodolac, ketorolac tromethamine, acetylsalicylic acid, sodium salicylate, diflunisal, sulindac, tolmetin sodium, mefanamic acid, meclofenamate sodium, fenoprofen and mixtures thereof.

A non-limiting list of opiod drugs contemplated for such a use includes codeine, morphine sulfate, hydroxymorphone, hydrocodone, oxycodone, meperidine and mixtures thereof.

A non-limiting list of antidepressant drugs contemplated for such a use includes amytriptyline HCl, amoxapine, desipramine HCl, doxepine HCl, imipramine HCl, maprotiline HCl, phenelzine sulfate, fluoxetine HCl, sertraline HCl, trazodone and mixtures thereof.

A non-limiting list of angiotensin converting enzyme inhibitors contemplated for such a use includes quinipril, enalapril, captopril, benazepril, ramipril, trandolapril, lisinopril, fosinopril and mixtures thereof.

A non-limiting list of diuretics contemplated for such a use includes benzthiazide, bumetanide, chlorthiazide, chlorthalidone, ethacrynic acid, furosemide, hydrochlorothiazide, hydroflumethiazide, metolazone, polythiazide, spironalactone, triameterene and mixtures thereof.

BRIEF DESCRIPTION OF THE DRAWINGS

FIG. 2 depicts the patterns of PMS symptoms experienced by patients.

FIG. 6 shows a comparison between the normal number of $AT_1$ receptors in male and female rats as compared with rats which have been ovariectomized and subsequently treated with estrogen and progesterone.

DETAILED DESCRIPTION OF THE INVENTION

Figure 1:
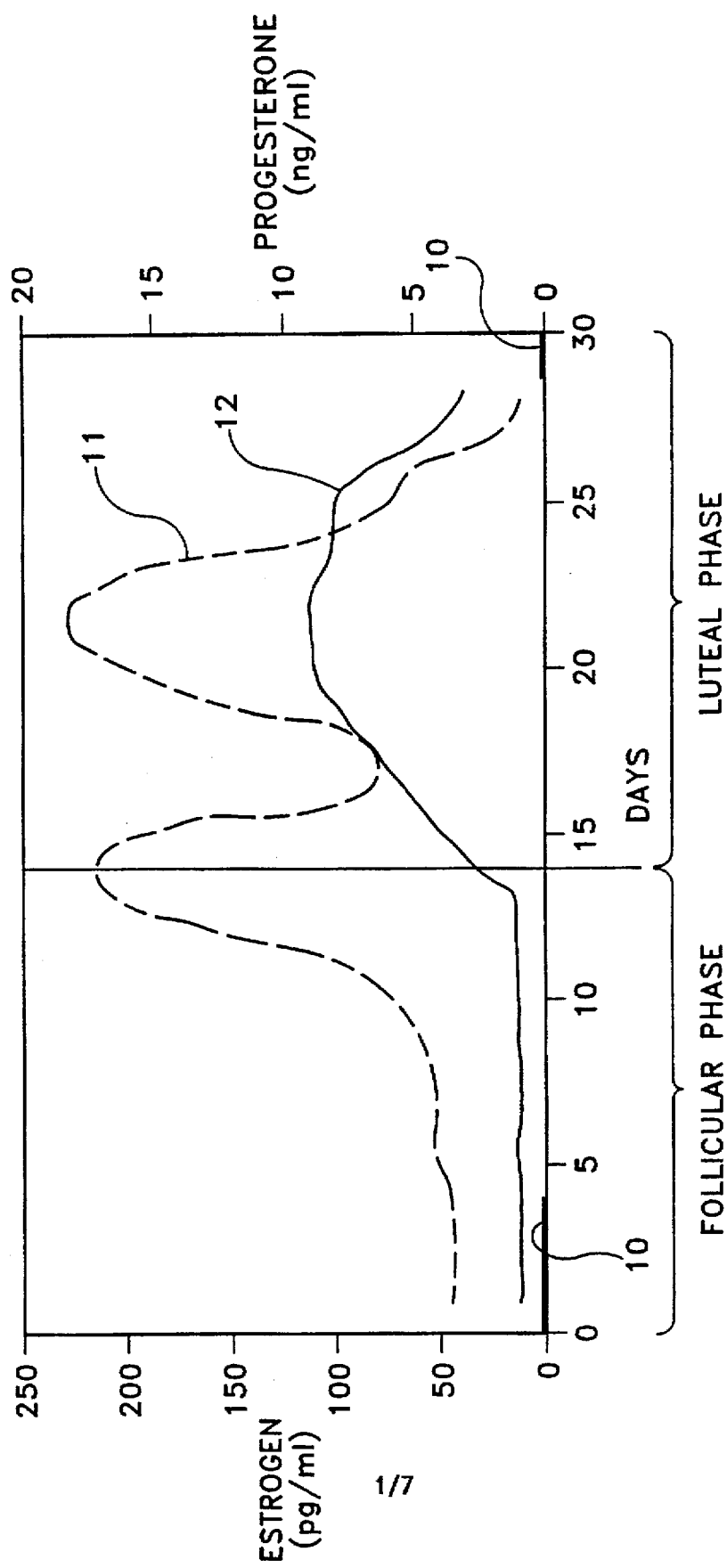
FIG. 1 illustrates the hormonal changes occurring during the human menstrual cycle.

The present invention is concerned with the treatment of sympathetically mediated pain as well as with the treatment of premenstrual syndrome (PMS) by the administration of $AT_1$ antagonists.

As stated previously, the hypothalamus is known to integrate hormonal activity and autonomic nervous system activity. Table I demonstrates the principal hypothalamic regulatory mechanism. (Ganong, W. F., *Review of Medical Physiology*, 14th ed., Appleton and Lange, 1989).

TABLE I

PRINCIPAL HYPOTHALAMIC REGULATORY MECHANISM

| FUNCTION | AFFERENTS FROM | INTEGRATING AREAS |
| --- | --- | --- |
| Temperature Regulation | Cutaneous Cold Receptors: Temperature-Sensitive Cells in Hypothalamus | Anterior Hypothalamus (Response to Heat) Posterior Hypothalamus (Response to Cold) |
| Neuroendocrine Control of Catecholamines | Emotional Stimuli, Probably via Limbic System | Dorsomedial and Posterior Hypothalamus |
| Vasopressin | Osmoreceptors, Volume Receptors, Others | Supraoptic and Paraventricular Nuclei |
| Oxytocin | Touch Receptors in Breast, Uterus, Genitalia | Supraoptic and Paraventricular Nuclei |
| Thyroid-Stimulating Hormone (Thyrotropin, TSH) via Thyrotropin-Stimulating Hormone (TRH) | Temperature Receptors, Perhaps Others | Dorsomedial Nuclei and Neighboring Areas |
| Adrenocorticotropic Hormones (ACTH) and B-Lipotrophin (B LPH) via Corticortropin-Releasing Hormone (CRH) | Limbic System (Emotional Stimuli);Reticular Formation ("Systemic" Stimuli); Hypothalamic or Anterior Pituitary Cells Sensitive to Circulating Blood Cortisol Level; Suprachiasmatic Nuclei (Diurnal Rhythm) | Paraventricular Nuclei |
| Follicle-Stimulating Hormone (FSH) and Luteinizing Hormone (LH) via Luteinizing-Hormone-Releasing Hormone (LHRH) | Hypothalamic Cells Sensitive to Estrogens; Eyes, Touch Receptors in Skin and Genitalia of Reflex Ovulating Species | Preoptic Area, Other Areas |
| Prolactin via Prolactin-Inhibiting Hormones (PIH) and Prolactin-Releasing Hormone (PRH) | Touch Receptors in Breasts, Other Unknown Receptors | Arcuate Nucleus, Other Areas (Hypothalamus Inhibits Secretion) |
| Growth Hormone via Somatostatin and Growth-Hormone-Releasing Hormone (GRH) | Unknown Receptors | Periventricular Nucleus, Arcuate Nucleus |
| "Appetitive" Behavior, Thirst Hunger | Osmoreceptors, Subfornical Organ "Glucostat" Cells Sensitive to Rate of Glucose Utilization | Lateral Superior Hypothalamus Ventromedial Satiety Center, Lateral Hunger Center; Also Limbic Components |
| Sexual Behavior | Cells Sensitive to Circulating Estrogen and Androgen, Others | Anterior Ventral Hypothalamus Plus (in the male) Piriform Cortex |
| Defensive Reactions, Fear, Rage | Sense Organs and Neocortex, Paths Unknown | In Limbic System and Hypothalamus |
| Control of Various Endocrine and Activity Rhythms | Retina via Retinohypothalalmic Fibers | Suprachiasmatic Nuclei |

It is also known that sympathetic functions and hypothalamic functions are regulated by $AT_1$ receptors. Further, changing levels of hormones such as ovarian hormones can change the density and function of the $AT_1$ receptors, as well as induce changes in the morphology of nerve cells throughout the central nervous system. In addition, the hypothalamus is the known regulator of autonomic activity. $AT_1$ receptor function is involved in autonomic nervous regulation due to the presence in the anatomically known regulating areas of the hypothalamus. The present invention hypothesizes that since hormones can modify the density of $AT_1$ receptors, they therefore modify the functioning of the sympathetic nervous system.

The menstrual cycle of the human female is divided into follicular and luteal phases. FIG. 1 shows the hormonal changes that occur during the menstrual cycle, such as estrogen 11 and progesterone 12. Days one through five are the days of the menses and correspond to the time when the menstrual flow is occurring. This period is sometimes referred to as the menstrual phase, as seen in FIG. 1 as menstrual phase 10. Premenstrual syndrome is the cyclic recurrence in the luteal phase of a combination of physical, psychological and/or behavioral symptoms which significantly impair social or occupational functioning. Most women experience symptoms for 1 to 14 days, usually beginning after ovulation which occurs approximately on day 14. Ninety percent (90%) of menstruating females exhibit some symptoms of PMS, but only 20–40% of patients are incapacitated to some degree or require therapy. Typically, PMS symptoms can be grouped, for example, as follows:

Affective/Cognitive Symptoms—i.e., changes in libido, unreasonable erratic behavior, lack of emotional control, tension, mood swings, restlessness, insomnia, feelings of guilt, low self image, distractable, inward anger, labile mood, irritability, cyclical depression and cyclical anxiety Autonomic Symptoms—i.e., hot or cold flashes, palpitations, chills, sweating and dizziness Somatic/Physical Symptoms—i.e., edema, breast tenderness, bloating of the abdomen or extremities, nausea, headache, pelvic or abdominal pain, and fatigue, muscular and joint pain FIG. 2 shows several symptom patterns reported by patients who suffer from PMS. These symptom patterns correspond with a time when there are high levels of both estrogen 11 and progesterone 12 as seen in FIG. 1. The symptoms usually remit with the onset of menses or within a few days afterwards. Also, as seen in FIG. 1, this remittance period is when levels of estrogen 11 and progesterone 12 are lowest.

Figure 3A:
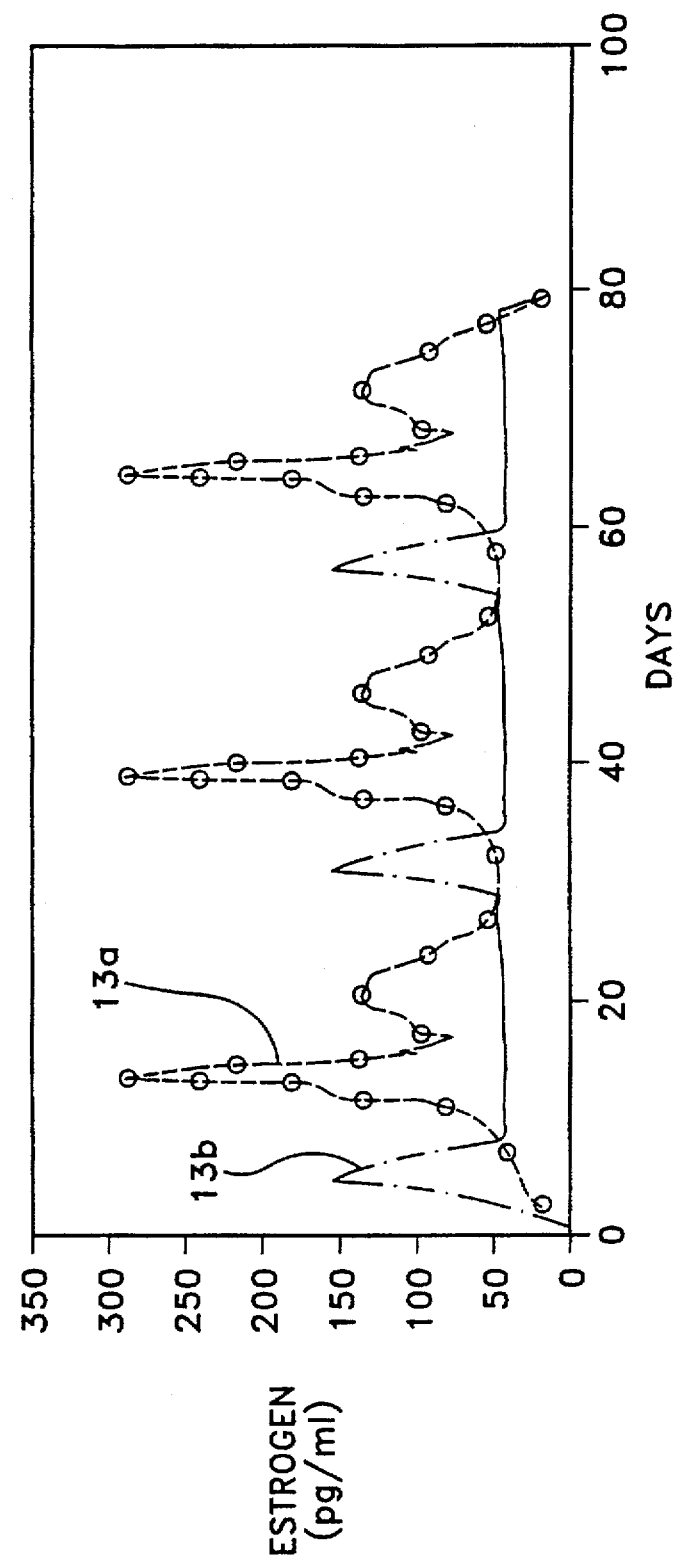
FIG. 3a and FIG. 3b depict the results of a study on circulating ovarian hormone levels showing patients treated with daily injections of GnRH agonist as compared with patients treated with placebo.
Figure 3B:
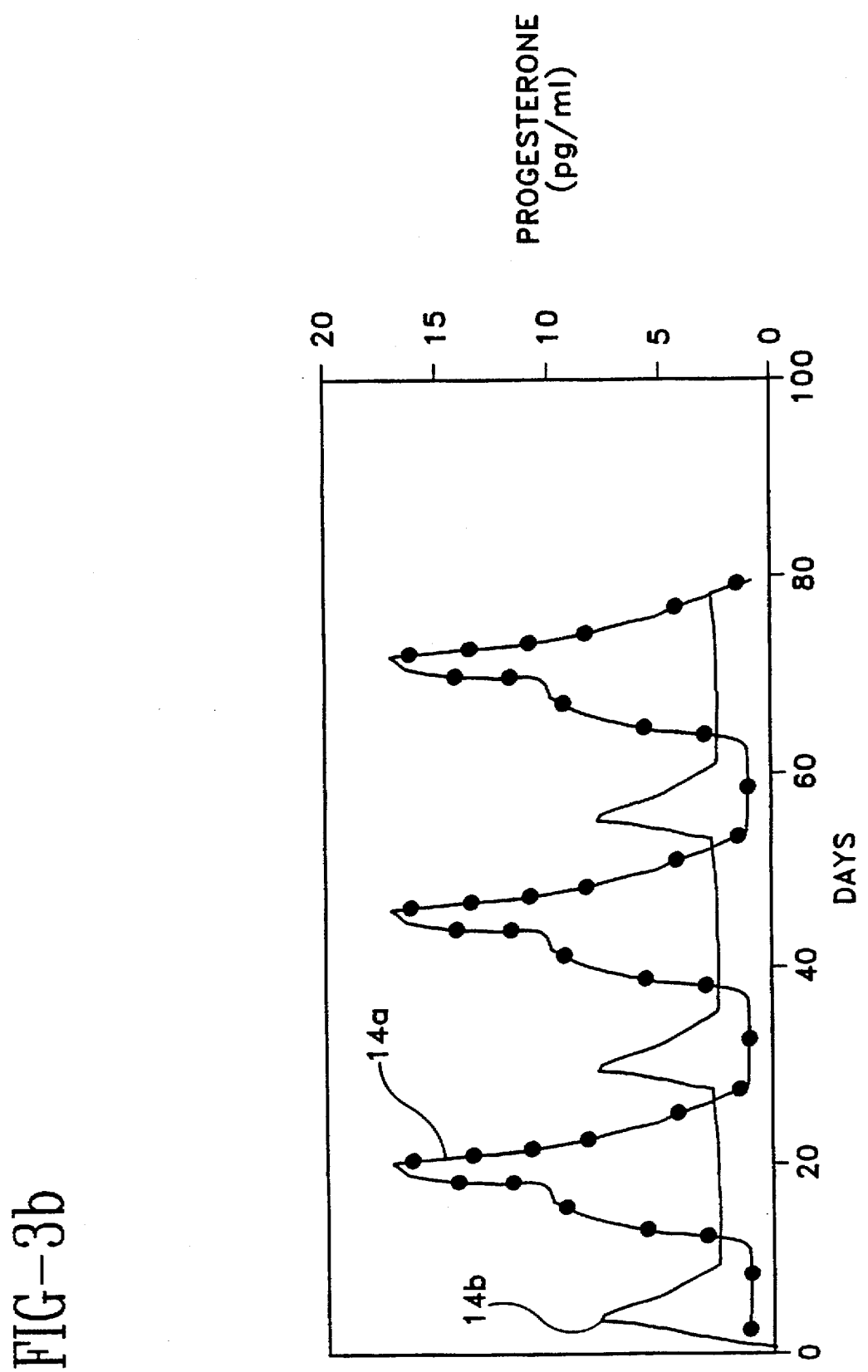
Figure 4:
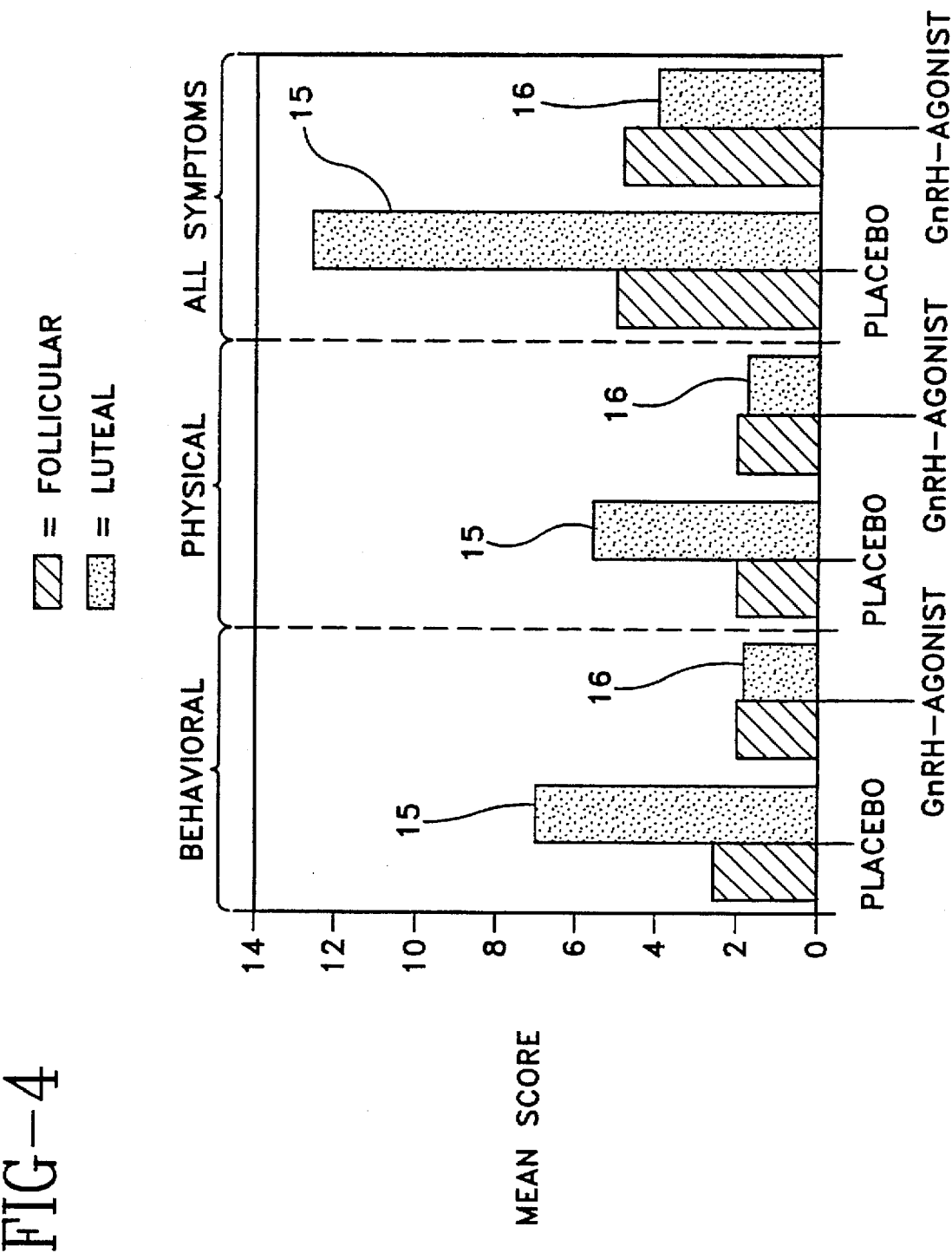
FIG. 4 depicts the effects of the same treatment as FIGS. 3a and 3b, showing the severity of PMS symptoms.

Three studies have clearly shown the role of ovarian hormones in PMS. Muse, et al. demonstrated that medical ovariectomy by daily injections of a GnRH agonist reduced the cyclic hormonal changes of estrogen and progesterone. (Muse, K. N.; Cetel, N. S.; Futterman, L. A.; Yen, S. S. C., *The Premenstrual Syndrome: Effects of "Medical Ovariectomy"*, N Engl J Med 311:1,345, 1984). Patients with moderate to severe PMS were treated with placebo or GnRH agonist for three months and measurements of hormone levels were made in the same patients during each course of therapy. The results of this study are shown in FIGS. 3a and 3b. FIG. 3a depicts the level of estrogen in placebo-treated patients 13a as compared to the level of estrogen in GnRH agonist-treated patients 13b. FIG. 3b depicts the level of progesterone in placebo-treated patients 14a as compared to the level of progesterone in GnRH agonist-treated patients 14b. In the patients receiving the GnRH agonist, the fluctuations in ovarian hormones were abolished when compared to the placebo-treated patients. This study also demonstrated the effects of reducing ovarian hormones on PMS symptoms, shown in FIG. 4. Typical physical and behavioral symptoms which were shown to occur during the luteal phase with placebo treatment 15 were significantly reduced with GnRH agonist treatment 16.

In a second study, Casper et al. demonstrated how a series of patients who underwent surgical ovariectomy showed complete resolution of PMS symptoms. (Casper, R. F.; Hearn, M. T., *The Effect of Hysterectomy and Bilateral Oophorectomy in Women with Severe Premenstrual Syndrome*, Am. J. Obstet. Gynecol. 162:105–9, 1990).

Finally, in a third study Hammarback et al. reported cyclical mood changes in postmenopausal patients receiving sequential estrogen and progesterone replacement therapy. (Hammarback, S.; Backstrom, T.; Holst, J.; von Schoultz, B.; Lyrenas, S., *Cyclical Mood Changes as in the Premenstrual tension Syndrome During Sequential Estrogen-Progesterone Postmenopausal Replacement Therapy*, Acta Obstet Gynecol Scand 64:393, 1985). Together these data clearly demonstrate the pivotal role of ovarian hormones in the genesis of PMS.

As noted above, PMS is characterized by multiple symptoms affecting various systems. If PMS is viewed as a single system dysfunction with a single pathophysiology and multiple manifestations, one is led to consider the hypothalamus as a connection between the cyclical changes and the symptoms. The hypothalamus regulates vegetative and endocrine function, and controls complex emotional and behavioral reactions by responding to various stimuli and integrating these stimuli into appropriate responses. A comparison of the hypothalamic functions and the symptoms of PMS suggests a correlation between the two, in that symptoms which are commonly seen in PMS are related to the types of responses and behaviors typically associated with the hypothalamus. A review of hypothalamic nuclei reveals that Angiotensin II and $AT_1$ receptors are present within the hypothalamus and that these receptors play a key role in regulating the multiple functions and coordinating actions of the hypothalamus.

Figure 5:
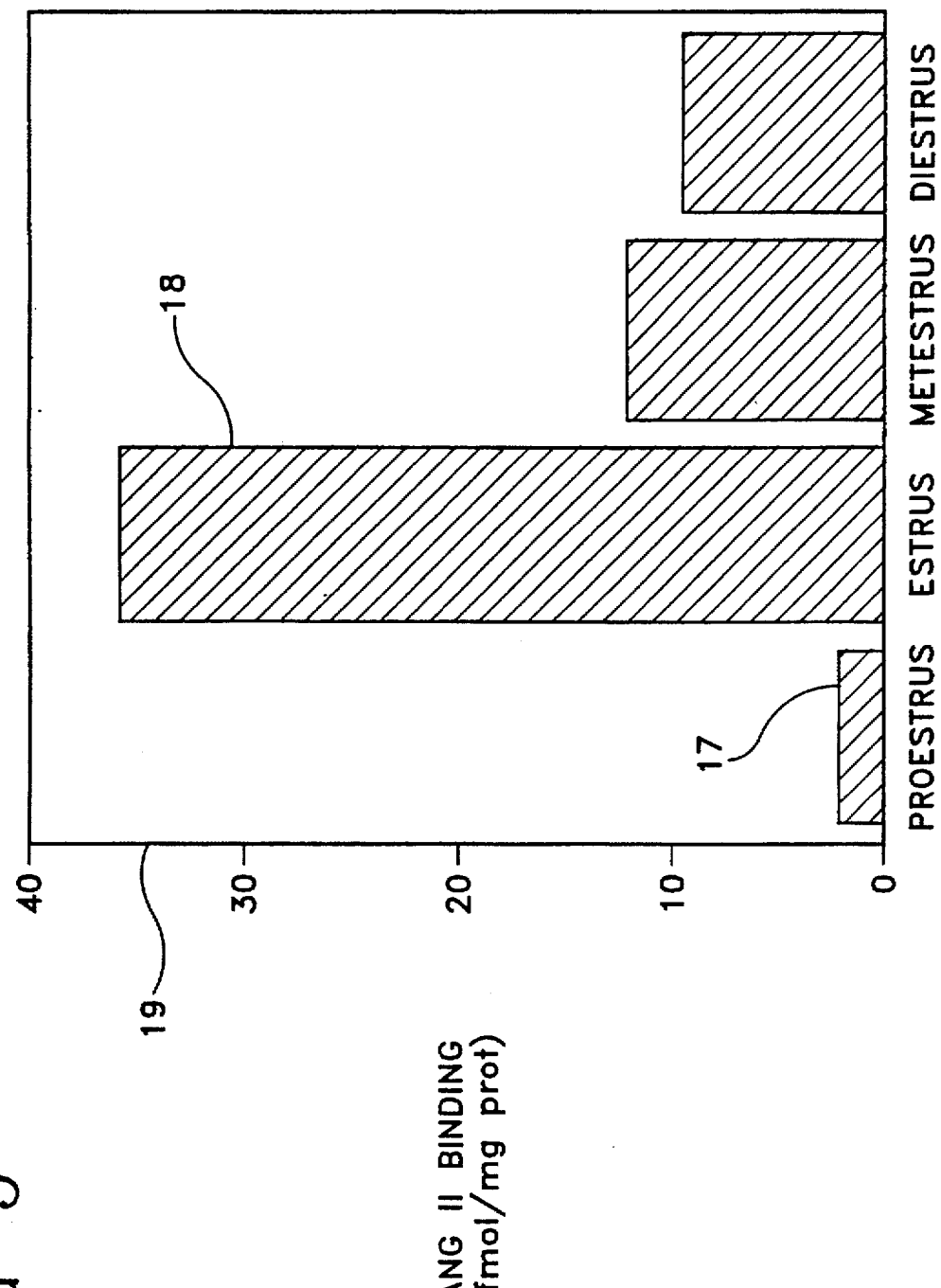
FIG. 5 shows the effects of cyclic ovarian hormone changes on $AT_1$ receptors.

Recent research has now shown that the hypothalamic $AT_1$ receptor density and functions are regulated by the cyclic changes in estrogen and progesterone. The $AT_1$ receptor is known to mediate the potent constrictor effects on smooth muscle, (i.e. vascular), to mediate the release of aldosterone from the adrenal cortex, and centrally activates or facilitates the activity of the sympathetic nervous system. How the $AT_1$ receptor mediates angiotensin functions is uncertain, but the distribution is different in various organs and tissues. It seems probable that ovarian hormones regulate Ang II receptor activity by altering their density or binding characteristics. To demonstrate this, Grove et al. administered estrogen and progesterone to rats after ovariectomy. (Grove, K. L.; Speth, R. C.; Sylvester, P. W.; Brisk, K. P., *Gonadal Steroids Alter Brain AnQiotensin II Receptors in Ovariectomized Rats*, Soc. For Neuroscience Abstracts, v 18, p. 1162, 1992). The rats treated with such ovarian hormones showed an increase in the number of Ang II receptors in the hypothalamic nuclei as compared with untreated rats. Further, as seen in FIG. 5, Seltzer et al. showed that the level of Ang II binding 19 and the number of $AT_1$ receptors in the dorsomedial arcuate nucleus of the hypothalamus of a rat is low at proestrus 17, which represents a low estrogen period, and increases significantly at estrus 18, which represents a high estrogen and progesterone period during the luteal phase. (Seltzer, A. et al., *Reproductive Hormones Modulate Angiotensin II Receptors in the Dorsomedial Arcuate Nucleus of the Female Rat*, Endocrinol v133, pp939–941, 1993). This was confirmed, as seen in FIG. 6, when ovariectomized animals treated with exogenous estrogen and progesterone showed a similar increase in $AT_1$ receptors (as depicted at level 20), while non-treated animals showed no such increase (as depicted at level 21).

The aforementioned references show a link between PMS and the cyclical ovarian hormone changes occurring in the female menstrual cycle. Further, the hypothalamus is known to regulate various physical and behavioral functions associated with PMS. Still further, the aforementioned references show that the density of $AT_1$ receptors in the hypothalamus varies with the phase of the ovarian cycle, and that estrogen and progesterone modulate $AT_1$ receptor density and function. When viewed in light of each other, the present invention contemplates that $AT_1$ receptors are important mediators in producing the symptoms of PMS. It is therefore discovered that by intervening to modulate the function of the $AT_1$ receptors, an effective method of treatment for PMS is provided. The present invention accomplishes this effective treatment by administering an effective amount of an $AT_1$ antagonist to a female during the luteal phase or symptomatic period of a menstrual cycle.

It is further contemplated by the present invention that changes in the density of $AT_1$ receptors and the morphology of nerve cells have consequence in the perception and generation of pain. As described, pain in humans manifests itself in numerous ways, some of which are directly related to the functions of the sympathetic nervous system. The sympathetic nervous system undergoes adaptive reactions in the presence of pain, and, as mentioned above, an intimate interconnection exists between pain conducting nerve pathways and the sympathetic nervous system. As such, painful stimuli can produce many well-recognized pain responses that are controlled through the sympathetic nervous system, for example, sweating, tachycardia (rapid heart rate), and pupillary dilation. (Stanton-Hicks, M. "Pain and the Sympathetic Nervous System", *American Academy of Pain Medicine*, Pain Medicine Board Review Course, Feb. 17–19, 1995).

It is believed that the central nervous system adapts in the presence of pain under various pathological conditions, and that neurohumoral and morphological changes occur within the central nervous system as a result of this adaptation. It is further believed that an increased sensitivity to pain occurs as a result of the coalition of abnormal sensations, autonomic functions, somatomotor functions and endocrine responses. As a result, sympathetic outflow to an affected part of the body may actually generate pain, and spontaneous pain may in part be dependent on such sympathetic activity. The involvement of the sympathetic nervous system in pain is further suggested by the use of local injection of anaesthetic or surgical ablation of sympathetic nerves to relieve pain. For example, chemically or thermoelectrically performed sypathectomy is used to treat chronic lumbar disc pain or visceral pain due to cancer. (Bradley, K. C., *The Sypathetic Nervous System and Pain*, Advances in Pain Research and Therapy, v13, Raven Press, NY 1990).

Additionally, many painful disorders reflect variability in intensity in relation to the menstrual cycle, for example, rheumatoid arthritis, epilepsy and menstrual migraine. Menstrual migraine, in particular, shows a variability of the hypothalamic responses in the luteal phase of the female menstrual cycle. One of the changes in response includes a change in autonomic regulation. Painful disorders such as fibromyalgia, myofascial pain syndrome and chronic fatigue syndrome are eight to 20 times more common in females, typically those females between the ages of 25 to 45, which corresponds to the age group most commonly affected by PMS. In fibromyalgia, there is a documented abnormality in the dexamethasone suppression test which reflects a change in the hypothalamic-pituitary axis. (Bennett, R. M., *Textbook of Rheumatology*, 4th ed., W. B. Sanders Co., 1993).

Further, acute or chronic pain mediated by the sympathetic nervous system is known to occur in the body. Such pain can typically result from trauma, injury, surgery, lower back disorders, arthritis, and the like. In addition, various pain syndromes have a connection with the sympathetic nervous system, for example, fibromyalgia, myofascial pain syndrome, chronic pain syndromes, syndromes of menstrual migraine, pain resulting from injury, and pain syndrome unrelated to injury which might include symptoms such as headache, musculoskeletal pain, pain localized to one side of the body, lower back pain, complex regional pain syndrome and sympathetically maintained pain syndrome. Such pain syndromes can produce various physical manifestations within the body, for example, Raynaud phenomenon (severe vasoconstriction of the blood vessels in the fingers), edema, numbness, paresthesia (abnormal spontaneous sensations), allodynia (pain caused by non-painful stimuli) and sweating.

In all of the aforementioned pain syndromes as well as with PMS, the hypothalamus is responsible for some aspect of the generation of the syndrome. Further, it is clear that in all of the aforementioned pain syndromes as well as with PMS, sympathetic and hypothalamic function are disturbed. As mentioned, $AT_1$ receptors are present in the hypothalamus. Sympathetic function and hypothalamic function are known to be regulated by these $AT_1$ receptors, as is parasympathetic nerve function. Thus, the present invention contemplates that any changes in the density of $AT_1$ receptors and/or the morphology of nerve cells in the brain area will have an effect on the perception of pain as well as PMS, and consequentially effect any pain responses. In other words, it is the hypothalamus that determines the distress that an injured or sick person in pain experiences to a greater degree than just the sensory intensity of the pain.

$AT_1$ antagonists are drugs which are known for blocking $AT_1$ receptors. The present invention provides an effective method for the treatment of acute or chronic pain mediated by the sympathetic nervous system by administering an effective amount of an $AT_1$ antagonist. Further, the present invention provides an effective method for the treatment of PMS by administering to a female during the luteal phase or symptomatic period of the menstrual cycle an effective amount of an $AT_1$ antagonist. An effective amount is defined as that amount capable of reducing the $AT_1$ receptor activity sufficiently to provide relief for PMS or for acute or chronic pain mediated by the sympathetic nervous system.

$AT_1$ antagonists which are useful with the present invention for the treatment of PMS and for the treatment of pain include, without limitation, those selected from the group including: sodium 2-(6-((2-ethyl-5,7-dimethyl-3H-imidazo(4,5-b)pyridin-3-yl)methyl)quinolin-2-yl)benzoate; 4'-((1,4'-dimethyl-2'-propyl(2,6'-bi-1H-benzimidazol)-1'-yl)methyl)-(1,1'-biphenyl)-2-carboxylic acid; 5-methyl-7-propyl-8-((2'-(1H-tetrazol-5-yl)biphenyl-4-yl)methyl)-1,2,4-triazolo(1,5-c)pyrimidin-2(3H)-one; 1-(N-(2'-(1H-tetrazol-5-yl)biphenyl-4-yl-methyl)-N-valerolylaminomethyl)cyclopentane-1-carboxylic acid; 1-((2'((i-pentyloxycarbonylamino)sulfonyl)-3-fluoro-(1,1'-biphenyl)-4-yl)methyl)-5-(2-(N-butyryl-N-pyridin-3-ylamino)propionyl)-4-ethyl-2-propyl-1H-imidazole, potassium salt; 4-ethyl-2-n-propyl-1-((2'-(1H-tetrazol-5-yl)biphenyl-4-yl) methyl)imidazole-5-carboxylic acid; 1H-Imidazole-5-carboxylic acid, 4-(pentafluoroethyl)-2-propyl-1-((2'-1H-tetrazol-5-yl)(1,1'-biphenyl)-4-yl)methyl-(CAS); 1H-imidazole-5-methanol, 2-butyl-4-chloro-1-((2'-(1H-tetrazol-5-yl)(1,1'-biphenyl)-4-yl)methyl)-, monopotassium salt (CAS); 3-((2'carboxybiphenyl)-4-yl)methyl)-2-cyclopropyl-7-methyl-3H-imidazo(4,5-b)pyridine; 1H-imidazole-5-carboxylic acid, 1-((3-bromo-2-(1H-tetrazol-5-yl)phenyl)-5-benzofuranyl)methyl)-2-butyl-4-chloro-(CAS); 2-butyl-4-chloro-1((2'-(1H-tetrazol-5-yl) (1,1'-biphenyl)-4-yl)methyl)-1H-imidazole-5-carboxylic acid,-1-(ethoxycarbonyloxy)ethylester, K+ salt; 3-methoxy-2,6-dimethyl-4-((2'-(1H-tetrazol-5-yl)-1,1'-biphenyl-4-yl) methoxy)pyridine; 6-(benzoylamino)-7-methyl-2-propyl-3-((2'-(N-(3-methyl-1-butoxy)carbonylaminosulfonyl)(1,1')-biphenyl-4-yl)methyl)-3H-imidazo(4,5-b)pyridine; 6-(N-acetyl-N-methylamino)-2-propyl-3-(2'-tetrazol-5-yl)-biphen-4-yl)methyl)quinazolin-4-(3H)-one; 1,1-dimethylethyl-2-(4'-(1-(3-(5-butyl)-2-oxo-(2-trifylphenyl)-(1,3,4)-trazolyl)methyl)biphenyl)sulfonylaminocarboxylate; 5-((3,5-dibutyl-1H-1,2,4-triazol-1-yl)methyl)-2-(2-(1H-tetrazol-5-ylphenyl))pyridine; 2-n-butyl-4-spirocyclopentane-1-(((2'-tetrazol-5-yl)biphenyl-4-yl)methyl)-2-imidazolin-5-one; 3-(2-butyl-1-(4-carboxybenzyl)-1H-imidazol-5-yl)-2-(2-thienylmethyl)-2-(E)-propenoic acid; 6-butyl-2-(2-phenylethyl)-5-((2'-(1H- tetrazol-5-yl)(1,1'-biphenyl)-4-yl)methyl)-4(1H)-Pyrimidinone; 2,7-diethyl-5-((2'-(5-tetrazolyl)biphenyl-4-yl)methyl)-5H-pyrazolo(1,5-b)(1,2,4)triazole; 1H-imidazole-5-carboxylic acid, 1-((3-bromo-2-(2-(1H-tetrazol-5yl)phenyl)-5-benzofuranyl)methyl)-2-butyl-4-chloro-(CAS); 1H-benzimidazole-7-carboxylic acid, 2-ethoxy-1-((2'-(1H-tetrazol-5-yl)(1,1'-biphenyl)-4-yl)methyl)-, 1-(((cyclohexyloxy)carbonyl)oxy)ethyl ester,-(CAS); methyl 2-((4-butyl-2-methyl-6-oxo-5-((2'-(1H-tetrazol-5-yl)-(1,1'-biphenyl)-4-yl)methyl)-1(6H)-pyrimidinyl)methyl)-3-thiophencarboxylate; and (S)-N-valeryl-N-((2'-(1H-tetrazol-5-yl)biphenyl-4-yl)methyl)-valine; and mixtures thereof.

The administration of the $AT_1$ antagonist can be accomplished by any known method of drug administration. Preferably, the $AT_1$ antagonist is administered orally, parenterally, intravenously, intra-nasally, or epidurally. Dosage forms contemplated by the present invention include tablets, capsules, elixirs, suppositories, solutions, suspensions, and the like. Also contemplated by the present invention are time-release and/or delay release dosage forms, including conventional pharmaceutical carrier, excipients, dispersants and the like.

The dosage range for the $AT_1$ antagonist is preferably from about 0.5 mg to about 800 mg over a period of about twenty-four hours, more preferably, from about 0.5 mg to about 500 mg over a twenty-four hour period.

In alternate embodiments of the present invention, the $AT_1$ antagonist can be administered in combination with a variety of other compounds and pharmaceutical actives. For example, the $AT_1$ antagonists can be administered in combination with non-steroidal anti-inflammatory drugs (NSAID's), opiod drugs, antidepressant drugs, angiotensin converting enzyme (ACE) inhibitors, diuretics, and the like, or mixtures thereof.

A non-limiting list of NSAID's contemplated for such a use includes ibuprofen, diclofenac, piroxcam, naproxen sodium, naproxen, nambumetone, etodolac, ketorolac tromethamine, acetylsalicylic acid, sodium salicylate, diflunisal, sulindac, tolmetin sodium, mefanamic acid, meclofenamate sodium, fenoprofen and mixtures thereof. Preferable dosage ranges of these NSAID's when used in combination with the $AT_1$ antagonists are shown in Table II.

TABLE II

| TYPE OF NSAID DRUG | AMOUNT OF NSAID DRUG mg/24 hours | AMOUNT of $AT_1$ ANTAGONIST mg/24 hours |
|---|---|---|
| ibuprofen | 200–3200 | 0.5–800 |
| diclofenac | 100–150 | 0.5–800 |
| piroxcam | 10–20 | 0.5–800 |
| naproxen sodium | 825–1375 | 0.5–800 |
| naproxen | 500–1500 | 0.5–800 |
| nambumetone | 1000–2000 | 0.5–800 |
| etodolac | 600–1200 | 0.5–800 |
| ketorolac tromethamine | 40–150 | 0.5–800 |
| acetylsalicylic acid/sodium salicylate | 300–1800 | 0.5–800 |
| diflunisal | 250–1500 | 0.5–800 |
| sulindac | 150–400 | 0.5–800 |
| tolmetin sodium | 200–1800 | 0.5–800 |
| mefanamic acid | 675–1250 | 0.5–800 |
| meclofenamate sodium | 50–400 | 0.5–800 |
| fenoprofen | 200–3200 | 0.5–800 |

A non-limiting list of opiod drugs contemplated for such a use includes codeine, morphine sulfate, hydroxymorphone, hydrocodone, oxycodone, meperidine and mixtures thereof. Preferable dosage ranges of these opiod drugs when used in combination with the $AT_1$ antagonists are shown in Table III.

TABLE III

| TYPE OF OPIOD DRUG | AMOUNT OF OPIOD DRUG mg/24 hours | AMOUNT OF $AT_1$ ANTAGONIST mg/24 hours |
|---|---|---|
| codeine | 30–3600 | 0.5–800 |
| morphine sulfate | 2–600 | 0.5–800 |
| hydromorphone | 1–20 | 0.5–800 |
| hydrocodone | 5–25 | 0.5–800 |
| oxycodone | 5–30 | 0.5–800 |
| meperidine | 50–1200 | 0.5–800 |

A non-limiting list of antidepressant drugs contemplated for such a use includes amytriptyline HCl, amoxapine, desipramine HCl, doxepine HCl, imipramine HCl, maprotiline HCl, phenelzine sulfate, fluoxetine HCl, sertraline HCl, trazodone and mixtures thereof. Preferable dosage ranges of these antidepressant drugs when used in combination with the $AT_1$ antagonists are shown in Table IV.

TABLE IV

| TYPE OF ANTI-DEPRESSANT DRUG | AMOUNT OF ANTIDEPRESSANT DRUG mg/24 hours | AMOUNT OF $AT_1$ ANTAGONIST mg/24 hours |
|---|---|---|
| amytriptyline HCl | 50–100 | 0.5–800 |
| amoxapine | 50–300 | 0.5–800 |
| desipramine HCl | 25–200 | 0.5–800 |
| doxepine HCl | 25–200 | 0.5–800 |
| imipramine HCl | 30–200 | 0.5–800 |
| maprotiline HCl | 20–100 | 0.5–800 |
| phenelzine sulfate | 15–60 | 0.5–800 |
| fluoxetine HCl | 10–80 | 0.5–800 |
| sertraline HCl | 50–200 | 0.5–800 |
| trazodone | 50–400 | 0.5–800 |

A non-limiting list of angiotensin converting enzyme inhibitors contemplated for such a use includes quinipril, enalapril, captopril, benazepril, ramipril, trandolapril, lisinopril, fosinopril and mixtures thereof. Preferable dosage ranges of these ACE inhibitors when used in combination with the $AT_1$ antagonists are shown in Table V.

TABLE V

| TYPE OF ACE INHIBITOR | AMOUNT OF ACE INHIBITOR mg/24 hours | AMOUNT OF $AT_1$ ANTAGONIST mg/24 hours |
|---|---|---|
| quinipril | 10–80 | 0.5–800 |
| enalapril | 5–40 | 0.5–800 |
| captopril | 25–450 | 0.5–800 |
| benazepril | 10–40 | 0.5–800 |
| ramipril | 2.5–20 | 0.5–800 |
| trandolapril | 0.5–16 | 0.5–800 |
| lisinopril | 5–40 | 0.5–800 |
| fosinopril | 10–80 | 0.5–800 |

A non-limiting list of diuretics contemplated for such a use includes benzthiazide, bumetanide, chlorthiazide, chlorthalidone, ethacrynic acid, furosemide, hydrochlorothiazide, hydroflumethiazide, metolazone, polythiazide, spironalactone, triameterene and mixtures thereof. Preferable dosage ranges of these diuretics when used in combination with the $AT_1$ antagonists are shown in Table VI.

TABLE VI

| TYPE OF DIURETIC | AMOUNT OF DIURETIC mg/24 hours | AMOUNT OF $AT_1$ ANTAGONIST mg/24 hours |
|---|---|---|
| benzthiazide | 25–100 | 0.5–800 |
| bumetanide | 15–10 | 0.5–800 |
| chlorthiazide | 0.5–1000 | 0.5–800 |
| chlorthalidone | 12.5–100 | 0.5–800 |
| ethacrynic acid | 12.5–200 | 0.5–800 |
| furosemide | 10–80 | 0.5–800 |
| hydrochlorothiazide | 12.5–100 | 0.5–800 |
| hydroflumethiazide | 25–100 | 0.5–800 |
| metolazone | 0.5–20 | 0.5–800 |
| polythiazide | 1–4 | 0.5–800 |
| spironalactone | 25–400 | 0.5–800 |
| triameterene | 50–300 | 0.5–800 |

While the invention has been described herein in terms of certain preferred embodiments, those skilled in the art will recognize that various modifications can be made without departing from the scope of the present invention.

I claim:

1. A method of treating acute or chronic pain mediated by the sympathetic nervous system comprising administering to a patient an effective amount of an $AT_1$ antagonist.

2. A method according to claim 1, wherein said $AT_1$ antagonist is selected from the group consisting of sodium 2-(6-((2-ethyl-5,7-dimethyl-3H-imidazo(4,5-b)pyridin-3-yl)methyl)quinolin-2-yl)benzoate; 4'-((1,4'-dimethyl-2'-propyl(2,6'-bi-1H-benzimidazol)-1'-yl)methyl)-(1,1'-biphenyl)-2-carboxylic acid; 5-methyl-7-propyl-8-((2'-(1H-tetrazol-5-yl)biphenyl-4-yl)methyl)-1,2,4-triazolo(1,5-c)pyrimidin-2(3H)-one; 1-(N-(2'-(1H-tetrazol-5-yl)biphenyl-4-yl-methyl)-N-valerolylaminomethyl)cyclopentane-1-carboxylic acid; 1-(2'((i-pentyloxycarbonylamino)sulfonyl)-3-fluoro-(1,1'-biphenyl)-4-yl)methyl)-5-(2-(N-butyryl-N-pyridin-3-ylamino)propionyl)-4-ethyl-2-propyl-1H-imidazole, potassium salt; 4-ethyl-2-n-propyl-1-((2'-(1H-tetrazol-5-yl)biphenyl-4-yl) methyl)imidazole-5-carboxylic acid; 1H-Imidazole-5-carboxylic acid, 4-(pentafluoroethyl)-2-propyl-1-((2'-1H-tetrazol-5-yl)(1,1'-biphenyl)-4-yl)methyl-(CAS); 1H-imidazole-5-methanol, 2-butyl-4-chloro-1-((2'-(1H-tetrazol-5-yl)(1,1'-biphenyl)-4-yl)methyl)-, monopotassium salt (CAS); 3-((2'carboxybiphenyl-4-yl)methyl)-2-cyclopropyl-7-methyl-3H-imidazo(4,5-b)pyridine; 1H-imidazole-5-carboxylic acid, 1-((3-bromo-2-(1H-tetrazol-5-yl)phenyl)-5-benzofuranyl)methyl)-2-butyl-4-chloro-(CAS); 2-butyl-4-chloro-1((2'-(1H-tetrazol-5-yl)(1,1'-biphenyl)-4-yl)methyl)-1H-imidazole-5-carboxylic acid,-1-(ethoxycarbonyloxy)ethylester, K+ salt; 3-methoxy-2,6-dimethyl-4-((2'-(1H-tetrazol-5-yl)-1,1'-biphenyl-4-yl)methoxy)pyridine; 6-(benzoylamino)-7-methyl-2-propyl-3-((2'-(N-(3-methyl-1-butoxy)carbonylaminosulfonyl)(1,1')-biphenyl-4-yl)methyl)-3H-imidazo(4,5-b)pyridine; 6-(N-acetyl-N-methylamino)- 2-propyl-3-(2'-tetrazol-5-yl)-biphen-4-yl)methyl)quinazolin-4-(3H)-one; 1,1-dimethylethyl-2-(4'-(1-(3-(5-butyl)-2-oxo-(2-trifylphenyl)-(1,3,4)-trazolyl)methyl)biphenyl) sulfonylaminocarboxylate; 5-((3,5-dibutyl-1H-1,2,4-triazol-1-yl)methyl)-2-(2-(1H-tetrazol-5-ylphenyl))pyridine; 2-n-butyl-4-spirocyclopentane-1-(((2'-tetrazol-5-yl)biphenyl-4-yl)methyl)-2-imidazolin-5-one; 3-(2-butyl-1-(4-carboxybenzyl)-1H-imidazol-5-yl)-2-(2-thienylmethyl)-2-(E)-propenoic acid; 6-butyl-2-(2-phenylethyl)-5-((2'-(1H-tetrazol-5-yl)(1,1'-biphenyl)-4-yl)methyl)-4(1H)-Pyrimidinone; 2,7-diethyl-5-((2'-(5-tetrazolyl)biphenyl-4-yl)methyl)-5H-pyrazolo(1,5-b)(1,2,4)triazole; 1H-imidazole-5-carboxylic acid, 1-((3-bromo-2-(2-(1H-tetrazol-5yl)phenyl)-5-benzofuranyl)methyl)-2-butyl-4-chloro-(CAS); 1H-benzimidazole-7-carboxylic acid, 2-ethoxy-1-((2'-(1H-tetrazol-5-yl)(1,1'-biphenyl)-4-yl)methyl)-, 1-(((cyclohexyloxy)carbonyl)oxy)ethyl ester,-(CAS); methyl 2-((4-butyl-2-methyl-6-oxo-5-((2'-(1H-tetrazol-5-yl)-(1,1'-biphenyl)-4-yl)methyl)-1(6H)-pyrimidinyl)methyl)-3-thiophencarboxylate; and (S)-N-valeryl-N-((2'-(1H-tetrazol-5-yl)biphenyl-4-yl)methyl)-valine, and mixtures thereof.

3. A method according to claim 1, wherein said administering comprises administering at least one $AT_1$ antagonist orally.

4. A method according to claim 1, wherein said administering comprises administering at least one $AT_1$ antagonist intravenously.

5. A method according to claim 1, wherein said administering comprises administering at least one $AT_1$ antagonist intra-nasally.

6. A method according to claim 1, wherein said administering comprises administering at least one $AT_1$ antagonist epidurally.

7. A method according to claim 1, wherein said administering comprises administering at least one $AT_1$ antagonist in an amount from about 0.5 to about 800 mg over a period of about twenty-four hours.

8. A method according to claim 1, wherein said $AT_1$ antagonist is administered in combination with a drug selected from the group consisting of a non-steroidal anti-inflammatory drug, an opioid drug, an antidepressant drug, an angiotensin converting enzyme inhibitor, a diuretic, and mixtures thereof.

9. A method according to claim 8, wherein said non-steroidal anti-inflammatory drug is selected from the group consisting of ibuprofen, diclofenac, piroxcam, naproxen sodium, naproxen, nambumetone, etodolac, ketorolac tromethamine, acetylsalicylic acid, sodium salicylate, diflunisal, sulindac, tolmetin sodium, mefanamic acid, meclofenamate sodium, fenoprofen and mixtures thereof.

10. A method according to claim 8, wherein said opioid drug is selected from the group consisting of codeine, morphine sulfate, hydroxymorphone, hydrocodone, oxycodone, meperidine and mixtures thereof.

11. A method according to claim 8, wherein said antidepressant drug is selected from the group consisting of amytriptyline HCl, amoxapine, desipramine HCl, doxepine HCl, imipramine HCl, maprotiline HCl, phenelzine sulfate, fluoxetine HCl, sertraline HCl, trazodone and mixtures thereof.

12. A method according to claim 8, wherein said angiotensin converting enzyme inhibitor is selected from the group consisting of quinipril, enalapril, captopril, benazepril, ramipril, trandolapril, lisinopril, fosinopril and mixtures thereof.

13. A method according to claim 8, wherein said diuretic is selected from the group consisting of benzthiazide, bumetanide, chlorthiazide, chlorthalidone, ethacrynic acid, furosemide, hydrochlorothiazide, hydroflumethiazide, metolazone, polythiazide, spironalactone, triameterene and mixtures thereof.

14. A method of treating sympathetically mediated pain disorders comprising administering to a patient an effective amount of an $AT_1$ antagonist.

* * * * *